(12) United States Patent
Fujita et al.

(10) Patent No.: US 8,940,906 B2
(45) Date of Patent: Jan. 27, 2015

(54) NONLINEAR LUMINESCENT MOLECULE, FLUORESCENT STAIN, AND OBSERVATION METHOD

(75) Inventors: Katsumasa Fujita, Osaka (JP); Shin Mizukami, Osaka (JP); Kazuya Kikuchi, Osaka (JP); Satoshi Kawata, Osaka (JP); Shogo Kawano, Osaka (JP)

(73) Assignee: Osaka University, Osaka (JP)

( * ) Notice: Subject to any disclaimer, the term of this patent is extended or adjusted under 35 U.S.C. 154(b) by 430 days.

(21) Appl. No.: 13/380,749

(22) PCT Filed: Jun. 21, 2010

(86) PCT No.: PCT/JP2010/004122
§ 371 (c)(1),
(2), (4) Date: Dec. 23, 2011

(87) PCT Pub. No.: WO2010/150509
PCT Pub. Date: Dec. 29, 2010

(65) Prior Publication Data
US 2012/0107960 A1 May 3, 2012

(30) Foreign Application Priority Data
Jun. 26, 2009 (JP) ................................ 2009-152138

(51) Int. Cl.
*C07F 5/02* (2006.01)
*G01N 21/64* (2006.01)
*C09B 23/04* (2006.01)
*C09B 57/10* (2006.01)

(52) U.S. Cl.
CPC .............. *C07F 5/022* (2013.01); *C09B 23/04* (2013.01); *C09B 57/10* (2013.01); *G01N 21/6428* (2013.01); *G01N 2021/6432* (2013.01); *G01N 2021/6439* (2013.01); *G01N 2021/6441* (2013.01)
USPC ........................................................ 548/110

(58) Field of Classification Search
None
See application file for complete search history.

(56) References Cited

U.S. PATENT DOCUMENTS

2008/0269486 A1  10/2008  Zhou et al.

FOREIGN PATENT DOCUMENTS

| JP | 05-297426 A | 11/1993 |
|---|---|---|
| JP | 08-220574 A | 8/1996 |
| JP | 2002265443 A1 | 9/2002 |
| JP | 2005284107 A | 10/2005 |
| JP | 2007-219024 A | 8/2007 |
| JP | 2008-18665 | 1/2008 |
| WO | 2006/061947 A1 | 6/2006 |
| WO | 2007055364 A1 | 5/2007 |
| WO | 2009/096432 A1 | 8/2009 |

OTHER PUBLICATIONS

Strehmel, et al., Two-Photon Physical Organic, and Polymer Chemistry: Theory, Techniques, Chromophore Design, and Applications: Advances in Photochemistry, 29:111 (2007) only pp. 111, 112, 225-233.*
International Search Report dated Jul. 20, 2010 from corresponding International Patent Application No. PCT/JP2010/004122-2 pages.
Max Born et al., "Principles of Optics", sixth edition, (Britain), The Press Syndicate of the University of Cambridge, 1959, p. 440.
Marius Albota et al., "Design of Organic Molecules With Large Two-Photon Absorption Cross Section", Science, vol. 281, p. 1653-1656 (1998).
Winfried Denk et al., "Two-Photon Laser Scanning Fluorescent Microscopy", Science, vol. 248, No. 4951, p. 73-79 (1990).
Stefan W. Hell et al., "Three-Photon Excitation in Fluorescent Microscopy" J. Biomed. Opt., vol. 1, p. 71-74 (1996).
Pekka E Hanninen et al., "Two and Multiphoton Excitation of Conjugate-Dyes Using a Continuous Wave Laser", Optics Commun, vol. 130, p. 29-33 (1996).
Jianfang Chen et al., "Far-Field Superresolution Imaging With Dual-Dye-Doped Nanoparticles", Opt. Lett., vol. 34, No. 12, p. 1831-1833 (2009).

* cited by examiner

*Primary Examiner* — Michael Barker
(74) *Attorney, Agent, or Firm* — Maier & Maier, PLLC

(57) ABSTRACT

The present invention relates to a nonlinear fluorescent molecule that generates a nonlinear fluorescence reaction by incidence of excitation light. This nonlinear fluorescence molecule includes donors and, and an acceptor that is coupled to the donors and. As the donor is excited by the incidence of the excitation light, electric charge moves from the donor to the acceptor. Then, the donor and the acceptor form a charge separated state. In a state in which the charge separated state is maintained, the donor fluoresces when transiting from an excited state to a ground state.

10 Claims, 6 Drawing Sheets

NONLINEAR LUMINESCENT MOLECULE, FLUORESCENT STAIN, AND OBSERVATION METHOD

RELATED APPLICATIONS

This is the U.S. national stage application which claims priority under 35 U.S.C. §371 to International Patent Application No.: PCT/JP2010/004122 filed Jun. 21, 2010, which claims priority to Japanese Patent Application No. 2009-152138 filed Jun. 26, 2009, the disclosures of which are incorporated by reference herein their entireties.

TECHNICAL FIELD

The present invention relates to a nonlinear luminescent molecule, a fluorescent stain, and an observation method.

BACKGROUND ART

In the field of medicine and biology or the like, in order to contribute to the clarification of biological function and pathology, it is extremely important to explore a microstructure in the living body. An optical microscope is frequently used for the observation of such biological sample. However, in the observation by the optical microscope, structure below half of a wavelength of illumination light cannot be observed due to the wave nature of light. Therefore, only not less than about 200 nm can be observed (NPL 1). For example, spatial resolution can be improved by using a laser beam of a shorter wavelength for illumination light. However, since there is a technical limit in reducing the wavelength of the laser beam, the improvement in the spatial resolution naturally has a limit.

As a method exceeding the abovementioned limit of light, there is a method suggested of using multiphoton excitation of a fluorescent material. However, since it is necessary to use light with a long wavelength for the multiphoton excitation, the substantial spatial resolution cannot be improved. Further, there are other methods suggested to exceed the limit of light using a complicated optical system or a luminescence mechanism of molecules. However, an observing object that can be applied is limited due to the particularity of a device and a material to use, it has not been successful to substantially improve the spatial resolution of the optical microscope. On the other hand, from importance of exploring the microstructure inside the living body, development of an optical observation method that can realize the spatial resolution exceeding the limit of light has been desired.

PTL 1 discloses a fluorescence microscope that can improve the spatial resolution without reducing the wavelength of the laser beam. In this fluorescence microscope, a nonlinear optical effect generated by saturation of fluorescence is used. Accordingly, it is possible to realize a fluorescence microscope with high spatial resolution without reducing the wavelength of the laser beam. However, with this fluorescence microscope, since a complicated control system must be used, introduction and employment thereof requires a great cost.

Moreover, the inventors have invented a nonlinear optical material that can improve the spatial resolution in advance of this application. This invention has been applied as Japanese Patent Application No. 2008-018665. According to this, a nonlinear optical effect can be realized by mixing and using a donor molecule and an acceptor molecule of the nonlinear optical material.

CITATION LIST

Patent Literature

PTL 1: International Patent Publication No. WO 2006/061947

Non Patent Literature

NPL 1: Max Born et al., "Principles of Optics", sixth edition, (Britain), The press syndicate of the University of Cambridge, 1959, p 440

SUMMARY OF INVENTION

Technical Problem

In a conventional multiphoton excitation fluorescence microscope, a laser beam which has a wavelength greater than certain wavelength must be used for excitation light for generating a nonlinear optical effect. Accordingly, since the wavelength of the laser beam cannot be reduced in principle, substantial spatial resolution cannot be improved.

A purpose of the present invention is to provide a nonlinear luminescent molecule which realizes the spatial resolution exceeding the limit of the wavelength of the excitation light in optical observation using the nonlinear optical effect.

Solution to Problem

A nonlinear luminescent molecule according to a first aspect of the present invention for generating a nonlinear fluorescence reaction by incidence of excitation light that includes one or more donors and one or more acceptors, in which the one or more donors include a first donor, the one or more acceptors include a first acceptor that is coupled to the first donor, the first donor and the first acceptor form a charge separated state by electric charge moving from the first donor to the first acceptor as either one of the first donor and the first acceptor being excited by the incidence of the excitation light, and in a state in which the charge separated state is maintained, one of the donor and the acceptor which has not formed the charge separated state fluoresces when transiting from an excited state to a ground state. Accordingly, as a plurality of excitation light photons are required in order to obtain one fluorescence photon, a nonlinear fluorescence reaction can be realized.

The nonlinear luminescent molecule according to a second aspect of the present invention, in which an order of a nonlinear response is determined by a number of the donor and a number of the acceptor. Accordingly, an order of a nonlinear response of the nonlinear luminescent molecule can be controlled.

The nonlinear luminescent molecule according to a third aspect of the present invention, in which the number of the donor is greater than the number of the acceptor, and the donor is also excited by the incidence of the excitation light, the donor and the acceptor form the charge separated state by the electric charge moving from the excited donor to the acceptor, and in the state in which the charge separated state is maintained, the donor not forming the charge separated state fluoresces when transiting from the excited state to the ground state. Accordingly, it is possible to obtain the nonlinear fluorescence photon to which a fluorescence photon is emitted by the donor.

The nonlinear luminescent molecule according to a fourth aspect of the present invention, in which the number of the acceptor is greater than the number of the donor, and the acceptor is also excited by the incidence of the excitation light, the donor and the acceptor form the charge separated state by the electric charge moving from the donor to the excited acceptor, and in the state in which the charge separated state is maintained, the acceptor not forming the charge separated state fluoresces when transiting from the excited state to the ground state. Accordingly, it is possible to obtain a nonlinear luminescent molecule to which a fluorescence photon is emitted by the acceptor.

The nonlinear luminescent molecule according to a fifth aspect of the present invention, in which the donor is excited by multiphoton absorption. Accordingly, since the nonlinear response order of the nonlinear luminescent molecule can be increased, the spatial resolution of optical observation can be further improved.

The nonlinear luminescent molecule according to a sixth aspect of the present invention, in which the acceptor is excited by multiphoton absorption. Accordingly, since the nonlinear response order of the nonlinear luminescent molecule can be increased, the spatial resolution of optical observation can be further improved.

A fluorescent stain in which the above nonlinear fluorescence molecule is dissolved in a solvent, and a sample to be a target of optical observation is dyed by the nonlinear fluorescent molecule dissolved in the solvent. Accordingly, as the sample can be dyed, the spatial resolution of the optical observation can be improved.

The fluorescent stain according an eighth aspect of the present invention, in which the nonlinear luminescent molecule is coupled to an additive for facilitating to fix the nonlinear luminescent molecule to the sample. Accordingly, as the sample can be easily dyed, the spatial resolution of the optical observation can be improved.

The fluorescent stain according to a ninth aspect of the present invention in which the above nonlinear fluorescent molecule adheres to a particle dispersed in a liquid, and the particle adhered to the sample to be the target of the optical observation. Accordingly, as the sample can be easily dyed, the spatial resolution of the optical observation can be improved.

The fluorescent stain according to a tenth aspect of the present invention, in which a biological sample is dyed by the nonlinear fluorescent molecule. Accordingly, as the biological sample can be easily dyed, the spatial resolution of optical observation can be improved.

An observation method of the sample according to an eleventh aspect of the present invention is an observation method of the sample dyed by the above fluorescent stain includes focusing a laser beam, which is excitation light, and irradiating the sample therewith, scanning to change a relative position between a focus of the laser beam and the sample, separating fluorescence generated by the irradiation of the laser beam from the laser beam and detecting it, and imaging the sample based on intensity of the detected fluorescence. Accordingly, the sample can be observed with high spatial resolution.

The observation method according a twelfth aspect of the present invention includes moving the focus of the laser beam in the sample along with an optical axis and detecting the fluorescence. Accordingly, the sample can be observed with high spatial resolution also in the depth direction.

The observation method according to a thirteenth aspect of the present invention includes detecting the fluorescence via a confocal optical system. Accordingly, the sample can be observed with higher spatial resolution.

Advantageous Effects of Invention

According to the present invention, in the optical observation using the nonlinear optical effect, it is possible to provide the nonlinear luminescent molecule that realizes high spatial resolution exceeding the limit of the wavelength of the excitation light.

DESCRIPTION OF EMBODIMENTS

Hereinafter, an exemplary embodiment to which the present invention can be applied is explained. The following explanation explains the exemplary embodiment of the present invention, and the present invention is not limited the following exemplary embodiment. In order to clarify the explanation, the following descriptions are omitted and simplified as appropriate. Moreover, a person skilled in the art would be able to easily modify, add, and convert each element in the following embodiment in the scope of the present invention. Note that the ones denoted by the same numerals in each drawing indicate similar elements, and explanation is omitted as appropriate.

Figure 1A:
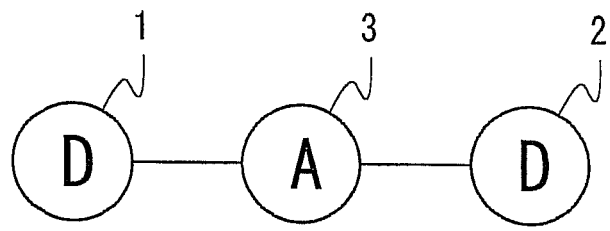
FIG. 1A is a view showing a luminescence process of a nonlinear luminescent molecule according to the present invention.

First, the principle of the nonlinear response of the nonlinear luminescent molecule according to the present invention is explained with a luminescence process as an example. FIGS. 1A to 1E are views showing a luminescence process of a nonlinear luminescent molecule when a laser beam, which is to be excitation light, is irradiated. In FIGS. 1A to 1E, D represents a donor of a ground state, A represents an acceptor of the ground state, D* represents a donor of an excited state, $D^+$ represents a donor in the charge separated state, and $A^-$ represents an acceptor of the charge separated state. As shown in FIG. 1A, this nonlinear luminescent molecule composes one molecule by donors 1 and 2 and an acceptor 3 being coupled. In this nonlinear luminescent molecule, the donors 1 and 2 fluoresce. In this exemplary embodiment, the nonlinear optical response is realized by using that electric charge generated by the light excited donor moves to the acceptor and the charge separated state is formed.

Figure 1B:
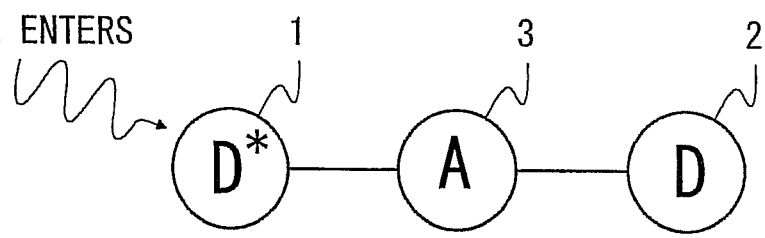
FIG. 1B is a view showing the luminescence process of the nonlinear luminescent molecule according to the present invention.

In the nonlinear luminescent molecule (FIG. 1A) in which all of the donors 1 and 2 and the acceptor 3 are in the ground state, for example, when a photon of a laser beam (hereinafter referred to as an excitation light photon), which is excitation light, enters the donor 1, the donor 1 is excited and electric charge is generated by photoinduction (FIG. 1B).

Figure 1C:
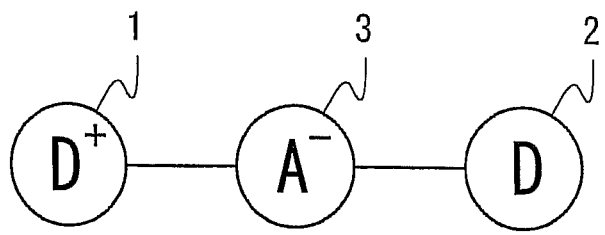
FIG. 1C is a view showing the luminescence process of the nonlinear luminescent molecule according to the present invention.
Figure 1D:
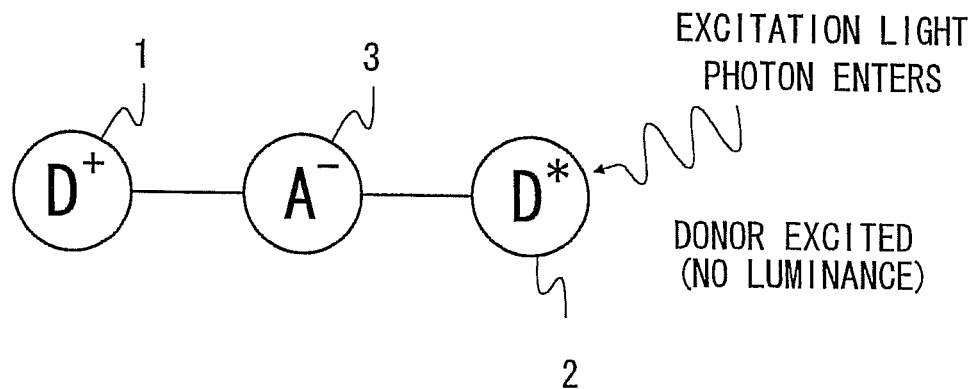
FIG. 1D is a view showing the luminescence process of the nonlinear luminescent molecule according to the present invention.

The electric charge generated by photoinduction moves to the acceptor 3 from the donor 1, and forms the charge separated state. (FIG. 1C). When the excitation light photon enters the donor 2 before this charge separated state is canceled, the donor 2 is excited (FIG. 1D). However, the donor 1 and the acceptor 3 have already formed the charge separated state. Accordingly, the electric charge generated in the donor 2 cannot move to the acceptor 3.

Figure 1E:
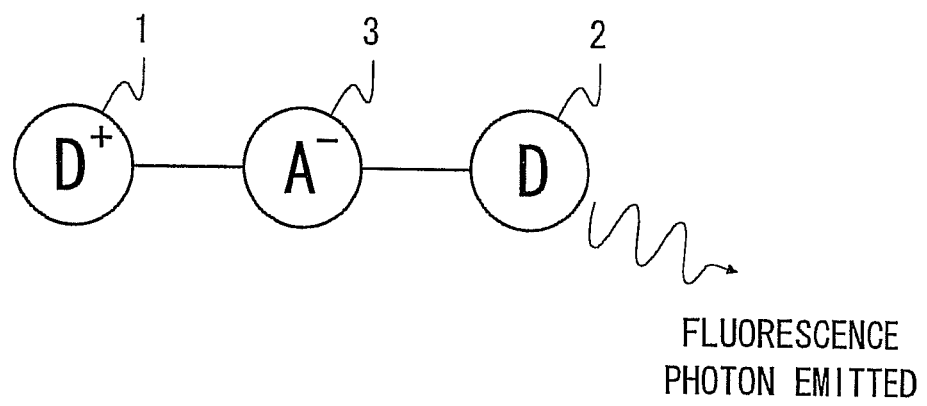
FIG. 1E is a view showing the luminescence process of the nonlinear luminescent molecule according to the present invention.

Therefore, the donor 2 fluoresces, emits a fluorescence photon, and transits to the ground state (FIG. 1E). Accordingly, since this nonlinear luminescent molecule absorbs two excitation light photons and emits one fluorescence photon, a second-order nonlinearity is generated in the relationship between the excitation light intensity and the fluorescence intensity.

Note that the nonlinear response of the nonlinear luminescent molecule is not limited to the process of the abovementioned FIGS. 1A to 1E. The case is shown above in which after the donor 1 and the acceptor 3 formed the charge separated state, the donor 2 is excited. However, after both the donor 1 and the donor 2 are excited, the donor 1 and the acceptor 3 can form the charge separated state and the donor 2 can fluoresce.

Although the nonlinear luminescent molecule shown in FIGS. 1A to 1E has a molecular structure in which two donors and one acceptor are coupled, by increasing the number of couplings between the donor and the acceptor, it is possible to realize the nonlinear luminescent molecule including higher-order nonlinearity. That is, in the nonlinear luminescent molecule in which (n+1) donors exist, n acceptors need to concern the formation of the charge separated state. Note that n is an integer greater than or equal to one. Specifically, in order for the donor to emit light, (n+1) excitation light photons must enter. Therefore, this nonlinear luminescent molecule shows the following (n+1)th order nonlinearity. Accordingly, the spatial resolution can be further improved.

Figure 3:
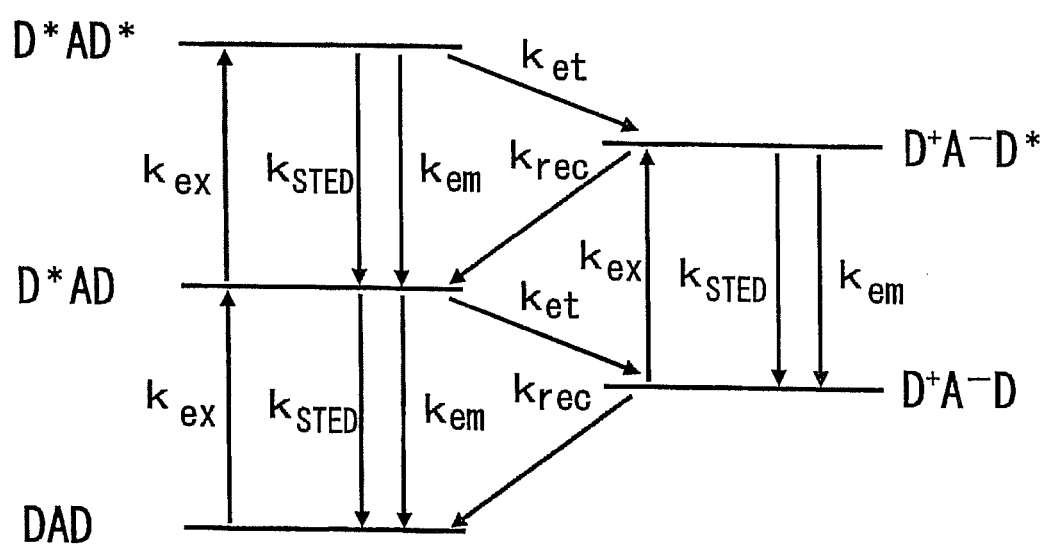
FIG. 3 is a view showing energy transition of the nonlinear luminescent molecule according to the present invention.

Note that the excitation light-fluorescence response of the above nonlinear luminescent molecule can be obtained from calculation. In this calculation method, the donors 1 and 2 and the acceptor 3 are represented using the two-level system model. FIG. 3 is a view showing energy transition combining a case when the donor will be the ground state or the excited state and a case when the donor and the acceptor form the charge separated state in the nonlinear luminescent molecule. As shown in FIG. 3, there can be five ways of states in this nonlinear luminescent molecule, and the states can be represented by the following five differential equations, respectively.

$$\frac{d[DAD]}{dt} =$$  [Expression 1]

$$-k_{ex}[DAD] + (k_{STED} + k_{em})[D^*AD] + k_{rec}[D^+A^-D]$$

$$\frac{d[D^*AD]}{dt} = k_{ex}[DAD] - (k_{STED} + k_{em} + k_{et} + k_{ex})$$

$$[D^*AD] + *(k_{STED} + k_{em})[D^*AD^*] +$$

$$(k_{STED} + k_{em})[D^*AD^*] + k_{rec}[D^+A^-D^*]$$

-continued $$\frac{d[D^*AD^*]}{dt} = k_{ex}[D^*AD] - (k_{STED} + k_{em} + k_{et})[D^*AD^*]$$

$$\frac{d[D^+A^-D]}{dt} = k_{et}[D^*AD] - (k_{ex} + k_{rec})[D^+A^-D] +$$

$$(k_{STED} + k_{em})[D^+A^-D^*]$$

$$\frac{d[D^+A^-D^*]}{dt} = k_{et}[D^*AD^*] + k_{ex}[D^+A^-D] +$$

$$(k_{rec} + k_{STED} + k_{em})[D^+A^-D^*]$$

D represents the donor of the ground state, A represents the acceptor of the ground state, $D^*$ represents the donor of the excited state, $D^+A^-$ represents the charge separated state. Further, $k_{ex}$ is a rate constant of excitation [s$^{-1}$], $k_{STED}$ is a rate constant of stimulated emission [s$^{-1}$], σ is an absorption cross-section [cm$^2$], $k_{em}$ is a rate constant of spontaneous emission [s$^{-1}$], $k_{et}$ is a rate constant of the charge separated state formation [s$^{-1}$], and $k_{rec}$ is a rate constant of charge recombination [s$^{-1}$].

In the calculation, $k_{ex}=\sigma \times \Phi$, $k_{STED}=\sigma \times \Phi$, $\sigma=1.85 \times 10^{-16}$, $k_{em}=1/(5.87 \times 10^{-9})$, $k_{et}=1/(1.00 \times 10^{-12})$, and $k_{rec}=1/(10.0 \times 10^{-9})$. Note that $\Phi[s \cdot cm^2]$ is an amount of incidence of excitation light photons per unit time and unit area.

Figure 4:
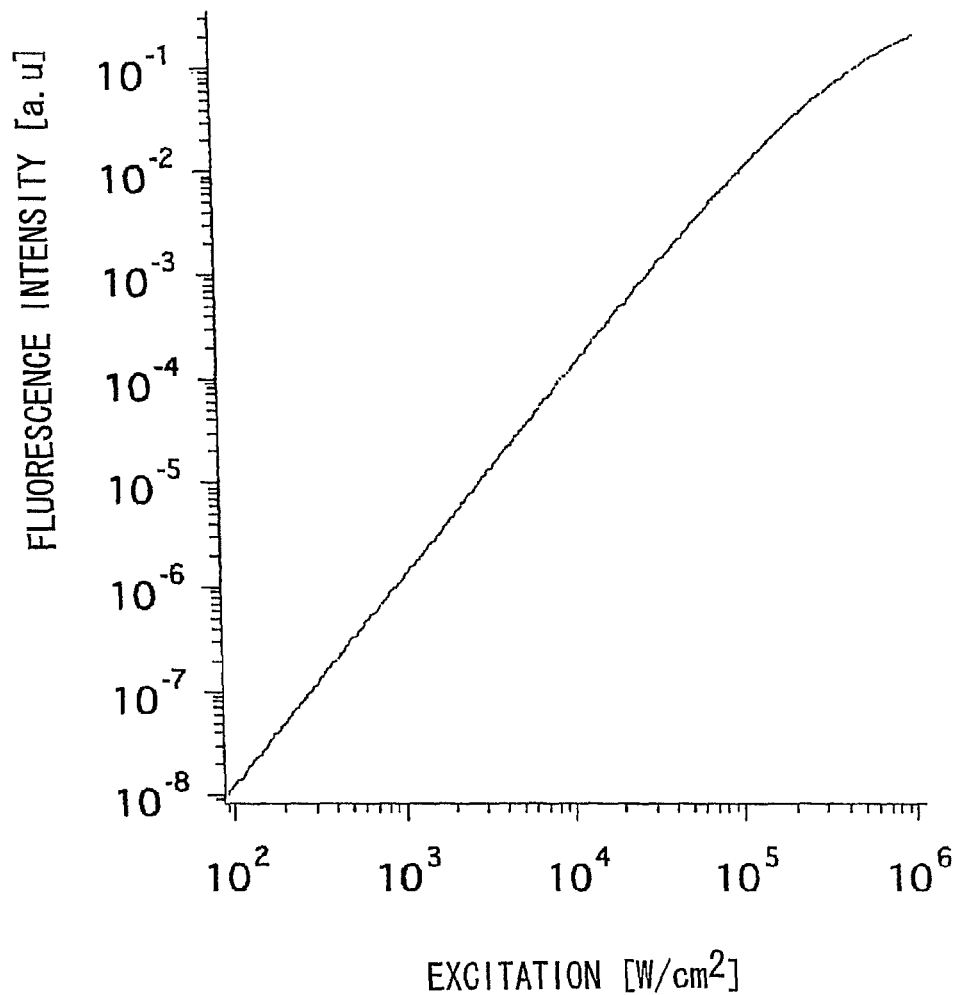
FIG. 4 is a graph showing a calculation result of excitation light intensity and fluorescence intensity of the nonlinear luminescent molecule according the present invention.

FIG. 4 is graph showing a result of abovementioned calculation. This graph is a log-log graph taking the excitation light intensity in the horizontal axis and the fluorescence intensity in the vertical axis, and can confirm that the fluorescence intensity nonlinearly increases along with an increase in the excitation light intensity. Accordingly, resolution of the optical observation can be improved by using this nonlinear luminescent molecule.

Moreover, in this nonlinear luminescent molecule, it may be a molecular structure in which the acceptor fluoresces. In this case, for example, it can be the molecular structure in which (m+1) acceptors and m donors are coupled. Note that, m is an integer greater than or equal to one. The acceptor is excited by incidence of the excitation light photon in this nonlinear luminescent molecule. Then, the charge separated state is formed by an electron moving to the excited acceptor from the donor. Accordingly, when m excitation light photons enter this nonlinear luminescent molecule, m charge separated states will be formed. When the excitation light photon enters the acceptor that does not concern the formation of the charge separated state before this charge separated state is cancelled, this acceptor is excited. This excited acceptor fluoresces, emits a fluorescence photon, and transits to the ground state. That is, in order for the acceptor to emit light, (m+1) photons must enter. Therefore, this nonlinear luminescent molecule will include (m+1)th order nonlinearity, and can improve the spatial resolution.

Moreover, the donor or the acceptor may be excited by multiphoton absorption. In this case, in order to obtain one fluorescence photon, more excitation light photons are needed. Accordingly, since the order of the nonlinear response can be further increased, it is advantageous from a viewpoint of improving the spatial resolution. In particular, it is effective in the excitation of the nonlinear luminescent molecule of the sample depths, and a microstructure inside the sample can be observed with high resolution.

Further, when the donor or the acceptor can be excited, a laser beam of any wavelength such as ultraviolet light laser, visible-light laser, or infrared light laser, can be used as excitation light, for example. As compared to a conventional multiphoton excitation fluorescence microscope that needs to use a laser beam of a long wavelength, in this exemplary embodiment, a short wavelength laser such as ultraviolet light can be used, thus it is effective in terms that substantial spatial resolution can be improved.

Next, usage of the abovementioned nonlinear luminescent molecule is explained. The nonlinear luminescent molecule according to this exemplary embodiment is used as fluorescence dye used for the optical observation of the biological sample, for example. With staining a microstructure in the sample by the nonlinear luminescent molecule, intensity of fluorescence generated by the molecules is used for constructing a fluorescence image of the sample. Then, it is possible to observe the microstructure in the living body with high spatial resolution.

According to this exemplary embodiment, this nonlinear luminescent molecule is dissolved in a solvent, and it is used as a solution. For example, a solution in which this nonlinear luminescent molecule is dissolved in water is used as the fluorescent stain. It is possible to realize the spatial resolution exceeding the limit of light by irradiating the sample dyed using this fluorescent stain with the laser beam, and observing the fluorescence intensity from the sample. Note that the solvent is not limited to water but other liquids can be used as the solvent as long as the sample can be dyed.

The above nonlinear luminescent molecule may not be used alone, however for example, it may be coupled and used with a predetermined additives such as protein in order to facilitate fixing to components such as a cell wall and a nucleus of the biological sample. Then, it is possible to increase the substantial concentration of the nonlinear luminescent molecule fixed to the biological sample. Accordingly, the fluorescence intensity when a laser beam, which is excitation light, is irradiated will be high, and it is effective in the point that a high contrast ratio is obtained. Further, it is also possible to selectively dye a particular component of the biological sample by appropriately selecting the additive. Then, it is possible to selectively observe a particular microstructure.

Additionally, the above nonlinear luminescent molecule may be adhered to particles or the like which are dispersed in liquid and used. According to this, the nonlinear luminescent molecules adhere to the biological sample by a unit of aggregate molecules that are adhered to the particles. Therefore, it is possible to increase the substantial concentration of the nonlinear luminescent molecules adhered to the biological sample. Accordingly, the fluorescence intensity when the laser beam, which is excitation light, is irradiated will be high, and it is effective in the point of obtaining a high contrast ratio.

Next, an observation method in this exemplary embodiment is explained. According to this exemplary embodiment, the laser beam is used as the excitation light. As for cross-section intensity distribution of the laser beam, the light intensity reaches its maximum at the spot center of the laser beam as in Gaussian distribution, for example. Then, the light intensity becomes lower away with its distance from the spot center. Therefore, when the biological sample dyed by the abovementioned nonlinear luminescent molecule is irradiated with the laser beam, strong fluorescence emission can be obtained from the spot center of the laser beam within the range including the light intensity in which the nonlinear luminescent molecule performs a nonlinear response. Accordingly, an effect equivalent to narrowing down the spot of the laser beam can be achieved. Then, it becomes possible to observe the microstructure of the biological sample exceeding a diffraction limit of the laser beam by observing this fluorescence intensity.

Moreover, a cheap continuous oscillation laser can be used as the excitation light by using this nonlinear luminescent molecule. Accordingly, an expensive pulse used for the conventional multiphoton excitation fluorescence microscope is unnecessary. Further, an existing general optical device can be used for the observation of the fluorescence intensity. Therefore, the biological sample can be observed with a cheap and simple optical system and laser system.

First Exemplary Embodiment

Figure 2:
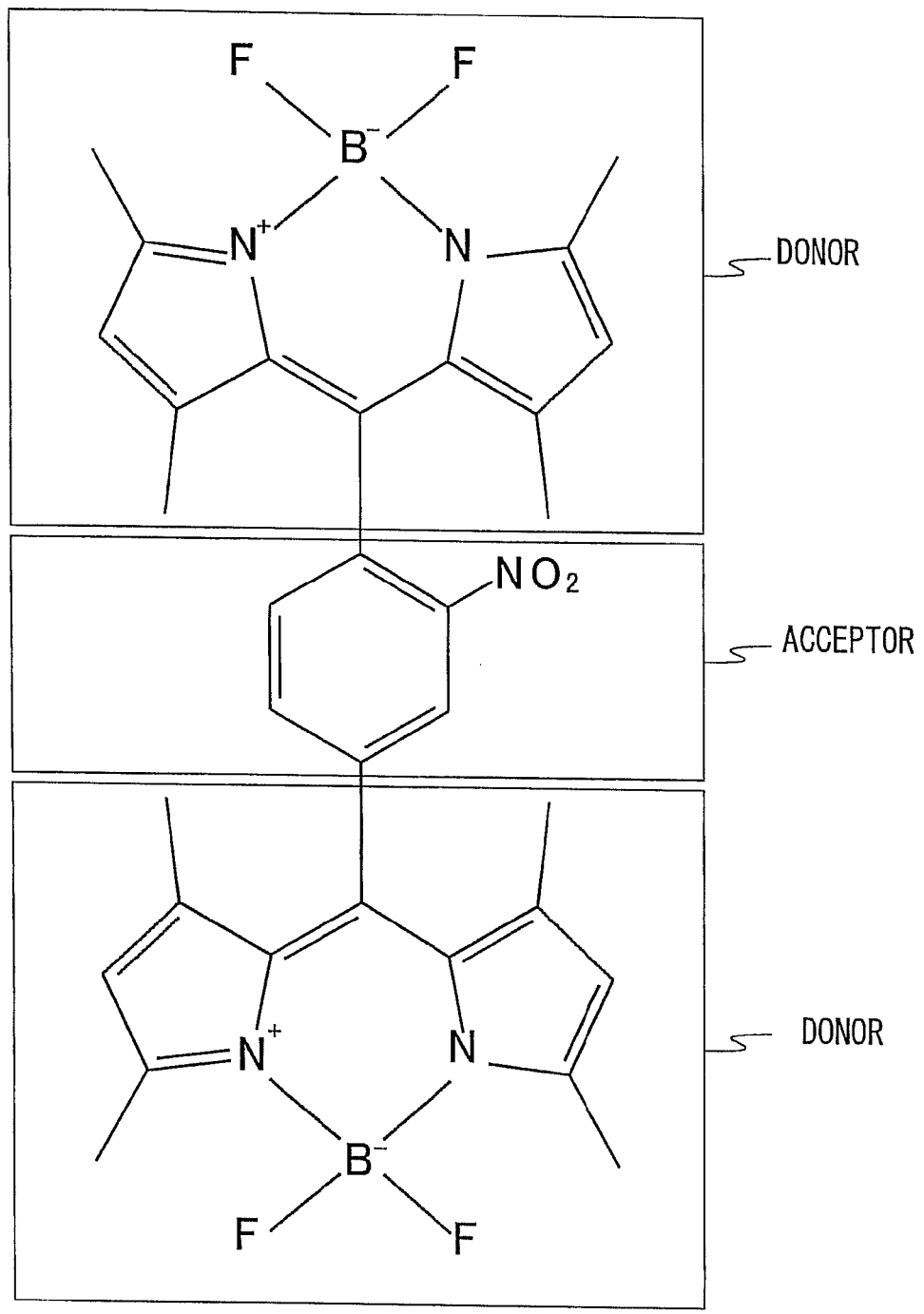
FIG. 2 is a view showing an example of a molecular structure of the nonlinear luminescent molecule according to the present invention.

An observation method of a sample using the abovementioned nonlinear luminescent molecule is explained. In this exemplary embodiment, the abovementioned nonlinear luminescent molecule is used as the fluorescence dye. Specifically, a fluorescent stain in which the nonlinear luminescent molecule dissolves dyes the biological sample, which is an observing object. Dyeing the biological sample can be performed by the immunostaining method, for example. This biological sample is observed, for example, with a laser scanning fluorescence microscope. FIG. 2 is a view showing an example of the molecular structure of the nonlinear luminescent molecule. In this exemplary embodiment, the nonlinear luminescent molecule which has the molecular structure shown, for example in FIG. 2, can be used.

Figure 5:
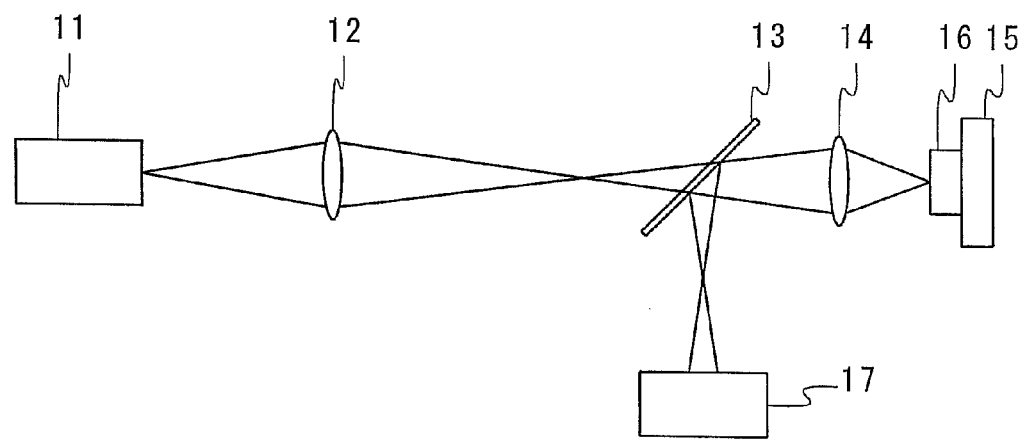
FIG. 5 is a block diagram schematically showing an optical system of a laser scanning fluorescence microscope according to a first exemplary embodiment.

FIG. 5 is a block diagram schematically showing an optical system of the laser scanning fluorescence microscope. As shown in FIG. 5, in this laser scanning fluorescence microscope, a laser beam, which is excitation light, is emitted from the laser light source 11. The emitted laser beam is refracted at a lens 12, and enters a dichroic mirror 13. The dichroic mirror 13 transmits the laser beam, which is the excitation light, and enters an objective lens 14. Then, the laser beam is collected on a biological sample 16, which is dyed by the nonlinear luminescent molecule, by the objective lens 14.

The biological sample 16 is set over the stage 15 that is capable of XYZ3 axis drive. For example, the biological sample 16 can be scanned by irradiating with a laser beam while driving the stage 15 in plane that is horizontal to an optical axis of the laser beam. The nonlinear fluorescent molecule fixed to the sample of the biological sample 16 fluoresces near the center of the laser beam spot, which is the excitation light. The fluorescence intensity changes according to the position where the laser beam, which is the excitation light, enters the biological sample 16.

The fluorescence passes through the objective lens 14, reflected by the dichroic mirror 13, and enters a detector 17. Then, the fluorescence intensity is detected by the detector 17. After that, a signal according to the fluorescence intensity is converted into an image.

According to this observation method, a microstructure smaller than the spot of the laser beam, which is the excitation light, can be observed. Therefore, the microstructure of the biological sample can be observed by the spatial resolution exceeding limit of light.

Other Exemplary Embodiment

Note that the present invention is not limited to the above exemplary embodiment, but can be modified as appropriate without departing from the scope. For example, three-dimensional observation of the biological sample can be performed by using the abovementioned nonlinear luminescent molecule. That is, the spatial resolution can be improved also in the depth direction by moving a focus of the laser beam, which is the excitation light, in the depth direction (optical axis direction) of the biological sample and observing the fluorescence luminescence intensity. Therefore, it is possible to obtain not only superficial information but also three-dimensional information of the biological sample.

Further, it is also possible to perform detection of the fluorescence intensity via a confocal optical system. Then, since the fluorescence in a focus of the laser beam can be selectively detected, the spatial resolution can be further improved.

Moreover, the nonlinear luminescent molecule shown in FIG. 2 is merely an example, and other molecular structures may be used as long as the donor and the acceptor can form the charge separated state.

Note that an observing object of the present invention is not limited to the biological sample. It is needless to say that other samples can be observed when the nonlinear luminescent object can be fixed or adhered to the sample and the fluorescence intensity can be measured.

In addition, the laser scanning fluorescence microscope according to the present invention is not limited to the configuration shown in the abovementioned FIG. 5. It is obvious that a laser scanning fluorescence microscope of a different configuration can be used as long as the observing object can be laser scanned.

The present application claims priority rights of and is based on Japanese Patent Application No. 2009-152138 filed on Jun. 26, 2009 in the Japanese Patent Office, the entire contents of which are hereby incorporated by reference.

INDUSTRIAL APPLICABILITY

The present invention can be applied to an optical observation method for observing the microstructure. That is, it is possible to realize the optical observation method that brings the spatial resolution exceeding the limit of light, and for example, perform observation of microstructure in the living body and localized biological molecule.

REFERENCE SIGNS LIST 1 and 2 DONOR
3 ACCEPTOR
11 LASER LIGHT SOURCE
12 LENS
13 DICHROIC MIRROR
14 OBJECTIVE LENS
15 STAGE
16 BIOLOGICAL SAMPLE
17 DETECTOR

The invention claimed is:

1. A molecule that generates nonlinear fluorescence, of formula:

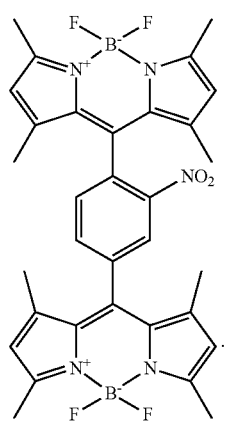 [SMILES: CC1=CC(C)=[N+]2C1=C(c1ccc(C3=C4C(C)=CC(C)=[N+]4[B-](F)(F)n4c(C)cc(C)c43)c([N+](=O)[O-])c1)c1c(C)cc(C)n1[B-]2(F)F]

2. A florescent stain, comprising a molecule of formula

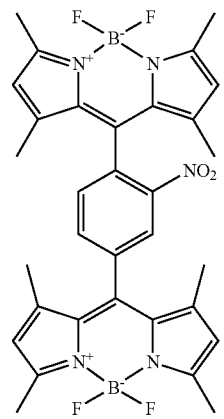 [SMILES: CC1=CC(C)=[N+]2C1=C(c1ccc(C3=C4C(C)=CC(C)=[N+]4[B-](F)(F)n4c(C)cc(C)c43)c([N+](=O)[O-])c1)c1c(C)cc(C)n1[B-]2(F)F]

dissolved in a solvent and generates nonlinear fluorescence in the presence of a sample that is being observed for nonlinear fluorescence under excitation light.

3. The florescent stain of claim 2, further comprising an additive which facilitates fixing of said stain to the sample.

4. The florescent stain of claim 2, which is adhered to a particle dispersed in a liquid, and said particle is adhered to the sample under observation.

5. The florescent stain of claim 2, wherein the sample is a biological sample.

6. A method of imaging a sample using nonlinear fluorescence, comprising: dying a sample with a stain containing a molecule of formula

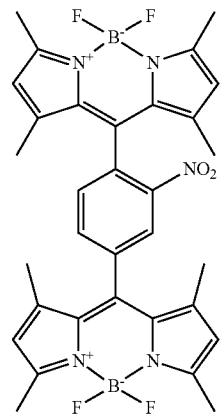 [SMILES: CC1=CC(C)=[N+]2C1=C(c1ccc(C3=C4C(C)=CC(C)=[N+]4[B-](F)(F)n4c(C)cc(C)c43)c([N+](=O)[O-])c1)c1c(C)cc(C)n1[B-]2(F)F]

dissolved in a solvent,
    irradiating the dyed sample with a laser beam to generate nonlinear fluorescence,
    scanning, to change position of the laser beam relative to the sample,
    separating fluorescence generated by said molecule and detecting it, and
    imaging the sample based on intensity of the detected fluorescence.

7. The method of claim 6, wherein the laser beam is a continuous oscillation laser beam.

8. The method of claim 6, further comprising moving a focus of the laser bean in the sample along an optical axis and imaging the sample in three dimensions.

9. The method of claim 6, further comprising detecting the fluorescence via a confocal optical system.

10. The method of claim 6, wherein the sample is a biological sample.

* * * * *